(12) United States Patent
Stamler et al.

(10) Patent No.: US 6,231,894 B1
(45) Date of Patent: May 15, 2001

(54) TREATMENTS BASED ON DISCOVERY THAT NITRIC OXIDE SYNTHASE IS A PARAQUAT DIAPHORASE

(75) Inventors: Jonathan S. Stamler, Chapel Hill, NC (US); Brian J. Day, Englewood, CO (US); Steven S. Gross, New York, NY (US); Owen W. Griffith, Milwaukee, WI (US)

(73) Assignees: Duke University, Durham, NC (US); National Jewish Medical and Research Center, Denver, CO (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/421,942

(22) Filed: Oct. 21, 1999

(51) Int. Cl.[7] .......................... A61K 33/00; A61K 31/44; A61K 31/04
(52) U.S. Cl. .......................... 424/718; 514/340; 514/610
(58) Field of Search .............................. 424/718; 514/610, 514/340

(56) References Cited

U.S. PATENT DOCUMENTS

| | | | |
|---|---|---|---|
| 4,593,097 | 6/1986 | Tomita et al. | 544/347 |
| 4,686,292 | 8/1987 | Migita et al. | 544/343 |
| 4,897,398 | 1/1990 | Gros et al. | 514/284 |
| 4,971,991 | 11/1990 | Umemura et al. | 514/410 |
| 5,272,146 | 12/1993 | Haugwitz et al. | 514/232.8 |
| 5,344,928 | 9/1994 | Masuya et al. | 544/37 |
| 5,407,940 | 4/1995 | Bisagni et al. | 514/285 |
| 5,441,941 | 8/1995 | Haugwitz et al. | 514/43 |
| 5,501,959 | 3/1996 | Lancaster et al. | 435/32 |
| 5,532,171 | 7/1996 | Motsenbocker | 436/533 |
| 5,847,004 | 12/1998 | Lai | 514/599 |
| 5,891,864 | 4/1999 | Han et al. | 514/45 |
| 5,908,842 | 6/1999 | Guthikonda et al. | 514/252 |
| 5,916,910 | 6/1999 | Lai | 514/423 |

OTHER PUBLICATIONS

Nemery, B., et al., Hum. Exp. Toxicol. 14, 308–309 (1995).
Hollinger, M. A., J. Pharmacol. Exp. Ther. 230, 292–294 (1984).
Ledwith, A., Accounts of Chemical Research, vol. 5, 133–139 (1972).
Watanabe, T., et al., J. Phys. Chem. 86, 2617–2619 (1982).
Pou, S. et al., J. Biol. Chem. 267, 24173–24176 (1992).
Berisha, H. I., et al., Proc. Natl. Acad. Sci. USA 91, 7445–7449 (1994).
Hogg, N., et al., in Methods of Molecular Biology, vol. 100, Nitric Oxide Protocols, ed. Titheradge, M. A., Humana Press, Totowa, N.J., 231–236 (1998).
Xia, Y., Proc. Natl Acad. Sci. USA 93, 6770–6774 (1996).
Dawson, T. M., et al., Proc. Natl Acad. Sci. USA, 88, 7797–7801 (1991).
Hope, B. T., et al., Proc. Natl Acad. Scie. USA, 88, 2811–2814 (Apr. 1991).
Vasquez–Vivar, J., et al., FEBS Lett 403, 127–130 (1997).
Miller, R. T., et al., Biochemistry 36, 15277–15284 (1997).
Vasquez–Vivar, J., et al., Biochemistry 36, 11293–11297 (1997).
Kobzik, L., et al., Am. J. Respir. Cell. Mol. Biol. 9, 371–377 (1993).

*Primary Examiner*—Raymond Henley, III

(57) ABSTRACT

Paraquat has been found to accept electrons from nitric oxide synthase (NOS) whereupon the reduced paraquat generates toxic $O_2^-$ and prevents NOS from giving electrons to arginine and thereby inhibits NO production. This is generalized for compounds with a redox potential greater than nitric oxide synthase. The compounds inhibit nitric oxide synthase and kill cells including NOS by generating $O_2^-$ and also by depriving the cells of the NO which they need. Applications include treating paraquat-induced injury and pathologically proliferating cells (tumors, restenosis benign prostatic hypertrophy, pulmonary hypertension, infective pathogens).

36 Claims, 5 Drawing Sheets

TREATMENTS BASED ON DISCOVERY THAT NITRIC OXIDE SYNTHASE IS A PARAQUAT DIAPHORASE

This invention was made at least in part with Government support under National Institutes of Health Grant No. RO1 HL59602.

TECHNICAL FIELD

The invention is directed to treating disorders in which reactive oxygen contributes to the pathology (e.g., paraquat-induced injury, stoke, adriamycin toxicity), to treating disorders characterized by pathologically proliferating cells containing a diaphorase, to inhibiting nitric oxide synthase, to constricting blood vessels, and for treating for NO depletion.

BACKGROUND OF THE INVENTION

Paraquat is a herbicide which damages the lungs, liver and kidneys, and produces toxicity by redox cycling with cellular diaphorases, thereby elevating intracellular levels of superoxide ($O_2^-$). Nitric oxide synthase (NOS) has been shown to participate in paraquat-induced lung injury. Current theory holds that nitric oxide (NO) generated by NOS reacts with $O_2^-$ generated by paraquat to produce the toxic peroxynitrite.

SUMMARY OF THE INVENTION

It has now been discovered that the "current theory" is incorrect and that rather NOS functions as a paraquat diaphorase. In other words, paraquat accepts electrons from nitric oxide synthase whereupon the reduced paraquat generates toxic $O_2^-$ and prevents NOS from giving electrons to arginine and thereby inhibits NO production thereby resulting in NO depletion. This is generalized for compounds with a redox potential greater than nitric oxide synthase. The compounds cause generation of $O_2^-$ and inhibit nitric oxide synthase and kill cells including NOS, by the combination of the increased $O_2^-$ and of depriving the cells of the NO which they need.

A first embodiment of the invention is directed to a method for treating paraquat-induced injury in a patient having such injury or preventing paraquat-induced injury in a patient at risk for such comprising administering to said patient a therapeutically effective amount of a nitric oxide synthase inhibitor that blocks electron transfer reactions of nitric oxide synthase.

A second embodiment of the invention is directed to a method of treating paraquat-induced injury or preventing paraquat-induced injury in a patient at risk for such comprising administering to said patient a therapeutically effective amount of NO providing compound.

A third embodiment of the invention is directed at a method for treating a patient having a disease in which nitric oxide synthase contributes to reactive oxygen production which causes tissue injury, comprising administering to said patient a therapeutically effective amount of nitric oxide synthase inhibitor that blocks electron transfer reactions of nitric oxide synthase and of NO providing compound.

A fourth embodiment of the invention is directed to a method for treating a patient having a disease where treatment with nitric oxide synthase inhibitor ameliorates symptoms of the disease but lowers the NO level to a cytotoxic level or where it is beneficial to supplement nitric oxide synthase inhibitor treatment with treatment with NO providing compound, comprising administering to said patient the nitric oxide synthase inhibitor in therapeutically effective amount, and also a therapeutically effective amount of NO providing compound.

A fifth embodiment of the invention is directed to a method of treating a patient with a disease characterized by pathologically proliferating cells containing nitric oxide synthase, comprising administering to said patient a therapeutically effective amount of a dipyridinum compound. In one aspect of this embodiment, agent that induces expression of nitric oxide synthase is also administered.

A sixth embodiment of the invention is directed to a method of treating a patient affected with a disorder in which reactive oxygen contributes to pathology, comprising administering to said patient a therapeutically effective amount of a nitric oxide synthase inhibitor which blocks generation of reactive oxygen from NOS. This embodiment is generic to the first embodiment.

A seventh embodiment of the invention is directed to a method of inhibiting nitric oxide synthase in a patient in need thereof, comprising administering to said patient a therapeutic amount of agent with a redox potential greater than nitric oxide synthase and an $LD_{50}$ greater than 1 $\mu M$ or 100 times the effective dose for systemic non-liposome or other non-local administration to inhibit nitric oxide synthase, and optionally to provide therapeutic effect except required in those cases necessary for novelty therapeutic amount of NO providing compound.

An eighth embodiment of the invention is the seventh embodiment where the patient is affected with a disorder characterized by pathologically proliferating cells containing nitric oxide synthase and the agent in inhibiting nitric oxide synthase accepts electrons from it to generate reactive oxygen to kill the pathologically proliferating cells.

A ninth embodiment of the invention is directed to a method of treating a patient affected with pathologically proliferating cells containing a diaphorase or a disease producing a diaphorase, comprising administering to said patient agent with a redox potential greater than the diaphorase and an $LD_{50}$ greater than 1 $\mu M$ or 100 times the effective dose for systemic non-liposome or other non-local administration to generate reactive oxygen and kill the pathologically proliferating cells, and optionally to provide therapeutic effect except required in those cases where necessary for novelty therapeutic amount of NO providing compound. This embodiment is generic to the eighth embodiment.

A tenth embodiment of the invention is directed to a method of treating a patient affected with pathologically proliferating cells, comprising causing overexpression of nitric oxide synthase in said patient, and administering to said patient a therapeutic amount of agent with redox potential greater than nitric oxide synthase and an $LD_{50}$ greater than 1 $\mu M$ or 100 times the effective dose for systemic non-liposome or other non-local administration. This embodiment is generic to the case of the fifth embodiment where agent that induces expression of nitric oxide synthase is also administered.

An eleventh embodiment of the invention is directed to treating a patient in need of constricting of blood vessels, said method comprising administering to said patient a therapeutically effective amount of agent with redox potential greater than nitric oxide synthase and an $LD_{50}$ greater than 1 $\mu M$ or 100 times the effective dose for systemic non-liposome or other non-local administration, and optionally to provide therapeutic effect except required in those cases where necessary for novelty therapeutic amount of NO providing compound.

A twelfth embodiment of the invention is directed to a method of treating patients for disorders where generation of $O_2^-$ provides benefit, comprising administering to said patient a amount of agent with a redox potential greater than nitric oxide synthase and an $LD_{50}$ greater than 1 μM or 100 times the effective dose for systemic non-liposome or other non-local administration to generate $O_2^-$ from nitric oxide synthase or other agents which otherwise generate $O_2^-$ in the patient and optionally to provide therapeutic effect except required in those cases where necessary for novelty NO providing compound. This embodiment is generic to all or portion of the fifth embodiment, the eighth embodiment and the ninth embodiment.

A thirteenth embodiment of the invention is directed to a method of determining nitric oxide synthase containing cells comprising the steps of adding a superoxide generating sufficient amount of paraquat to a suspension of cells and assaying for superoxide, with detecting of superoxide in the assay indicating the presence of nitric oxide synthase-containing cells.

A fourteenth embodiment of the invention is directed to a method for determining nitric oxide synthase deficient cells and thereby selecting for them, comprising adding paraquat to a suspension of cells in an amount to provide a concentration of paraquat ranging from 25 μM to 8 mM, thereby to kill nitric oxide synthase-containing cells and leave nitric oxide synthase deficient cells.

The term "paraquat-induced injury" is used herein to mean the lung, liver and or kidney injury normally associated with paraquat toxicity.

The term "patient" is used herein to mean mammal including a human.

Compounds are described above as having an $LD_{50}$ greater than 1 μM or 100 times the effective dose for systemic non-liposome or other non-local administration. Thus the compounds may be such that the effective dose may be equal to or greater than (e.g., even twice) the $LD_{50}$ when topically infused or locally administered or delivered by liposome. The $LD_{50}$ referred to is that in the species of the patient being treated.

The term "NO providing compound" is used herein to mean NO or compounds which contain NO or are converted to contain NO and generate NO or a bioactive NO equivalent in the patient or which raise endogenous NO levels in the patient or which otherwise generate NO in the patient. The term "agent with a redox potential greater than nitric oxide synthase" is used herein to mean agent susceptible to one or two electron reduction by nitric oxide synthase (plus NADPH).

DETAILED DESCRIPTION

Figure 1A:
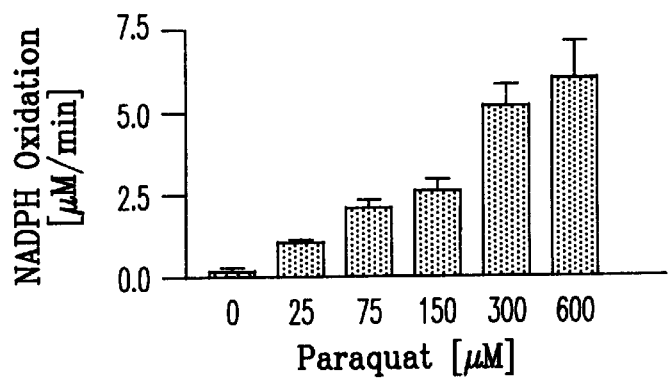
FIG. 1(a) is a graph of paraquat concentration versus NADPH oxidation and shows results of Background Example 1.

We turn now to the first embodiment which is directed to a method for treating paraquat-induced injury in a patient having such injury comprising administering to such patient a therapeutically effective amount (i e., an injury attenuating effective amount) of nitric oxide synthase inhibitor that blocks electron transfer reactions of nitric oxide synthase.

Examples of nitric oxide synthase inhibitors that block electron transfer reactions of nitric oxide synthase include L-NAME, other L-nitroarginine esters, L-nitroarginine, thiocitrulline and thiocitrilline esters. L-N-methylarginine, that is, L-NMMA, is not a nitric oxide synthase inhibitor that blocks electron transfer reactions of nitric oxide synthase.

In general, dosages for nitric oxide synthase inhibitors that block electron transfer reactions of nitric oxide synthase range from 0.01 μM to 10 mM. For the specific agents named above, dosage ranges are: L-NAME (0.01 μM to 10 mM, preferably 10 μM to 1 mM), L-nitroarginine (0.01 μM to 10 mM, preferably 10 μM to 1 mM), L-thiocitrulline (0.01 μM to 10 mM, preferably 10 μM to 1 mM), and L-thiocitrulline, methyl ester (0.01 μM to 10 mM, preferably 10 μM to 1 mM). These are end (obtained) concentrations, that is one would give a higher inhaled concentration (e.g., 100 nM) in order to achieve 1 mM, e.g., in the lung.

Routes of administration for the nitric oxide synthase inhibitors are, for example, topical, intravenous or inhaled. Intravenous route of administration is preferred for L-NAME.

Administration is continued as long as improvement occurs.

We turn now to the second embodiment, which is directed to a method of treating paraquat-induced injury comprising administering to said patient a therapeutically effective amount (i.e., an iny attenuating effective amount) of NO providing compound. The compounds should have an $LD_{50}$ greater than 1 $\mu$M. The NO providing compounds can be, for example, NO or NO donors or compounds which are converted to NO in the body or bioactive equivalent thereof (e.g., a redox related species) or compounds that raise endogenous NO levels or encapsulated nitric oxide synthase or its gene and can be antibiotics or other drugs which contain NO or are converted to contain NO in the body. NO donors are described in "Methods in Nitric Oxide Research," edited by Feelisch, M. and Stamler, J. S., John Wiley & Sons, New York, 1996 at pages 71–115 which are incorporated herein by reference. NO donors include compounds having the formula $RXNO_y$ where R is the parent compound, X is O, N, metal, S or C and y is 1 or 2. Exanples of NO donors are DETA NONOate; NO-substituted nitric oxide synthase inhibitors, e.g., NO-substituted tetracycline, NO-substituted cyclosporine, NO-substituted guanidino group in L-arginine based inhibitors including 1-methyl-3-nitro-1-nitrosoguanidine, $N^5$-nitroso-$N^G$-nitro-L-arginine and $N^5$-nitroso-$N^G$-nitro-L-arginine methyl ester, NO-substituted nitrogen in imidazole based nitric oxide synthase inhibitors including N-nitroso-imidazole, 1-nitroso-7-nitro-indazole and 1-nitroso-2-phenyl imidazole, and any other NO attachment to nucleophile in these inhibitors, NO-substituted BN 80933, NO-substituted iNOS dimerization inhibitors, and NO-substituted nitric oxide synthase inhibitors that block electron transfer reactions of nitric oxide synthase as described in the description of the third embodiment hereinafter; NO-substituted proteins, such as S-nitrosohemoglobin; other nitrosothiols; nitroprusside and other metal-NO containing compounds; and C-nitro and C-nitroso compounds. The NO-substituted BN 80933 has the formula

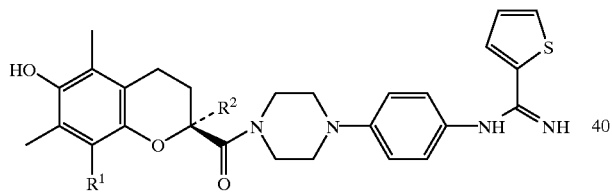

where none or one of $R^1$ of $R^2$ is $CH_3$ and one or both of $R^1$ and $R^2$ are selected from: —$(CH_2)_x$—SNO, —$(CH_2)_x$—ONO, —$(CH_2)_x$—$ONO_2$, and —$(CH_2)_x$—$N(R^3)$—$N(O^-)$—N=O where x is 1 to 4 and $R^3$ is alkyl cycloalkyl, aryl or alkylaryl of 1–12 carbon atoms. One kind of NO-substituted iNOS dimerization inhibitors have the formula

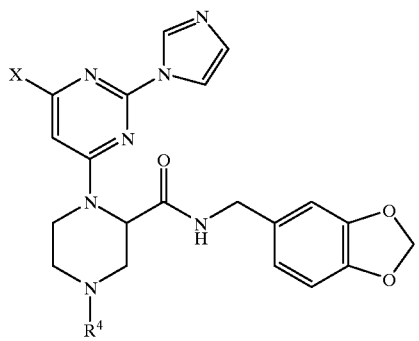

where X is H or Cl and $R^4$ is —$N(O^-)$—N=O or —NO or any of the substituents for $R^1$ and $R^2$ set forth above for NO-substituted BN 80933 except $CH_3$. Additionally, the other secondary amines can be nitrosated to yield N—NO derivatives. Other NO-substituted nitric oxide synthase inhibitors are S-nitroso-2-mercapto-ethylguanidine, S-(2-methylaminoethyl)-isothiourea NONOate, compounds of the formula

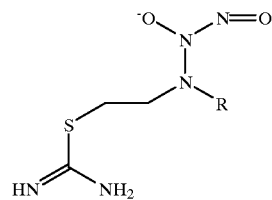

where R is $C_1$–$C_{12}$ alkyl cycloalkyl aryl or alkylaryl; compounds of the formula

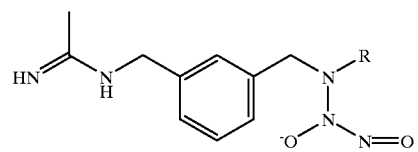

where R is $C_1$–$C_2$ alkyl, cycloalkyl aryl or alkylaryl; the compound having the formula

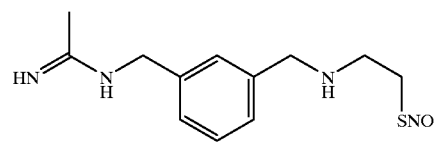

and the compounds

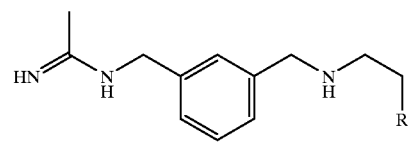

where R is —ONO or —$ONO_2$ Examples of compounds converted to NO in the body include, for example, nitrates, nitrites, C-nitro compounds, O-nitro compounds, S-nitro compounds, S-nitroso compounds, metronidazole, hydroxyurea and L-arginine. Examples of compounds that raise endogenous NO levels are HMG CoA reductase inhibitors, e.g., statins, e.g., lovastatin; thiols, e.g., N-acetylcysteine; angiotensin converting enzyme inhibitors, e.g., captopril; chemotherapeutic agents, e.g., tamoxifen or 5,6-dimethylxanthemone-4-acetic acid (5,6-MEXAA); mutated viruses and thereby inactivated and non-virulent, e.g., of the adenovirus class; estrogen; and superoxide dismutase; and/or mimetics. An example of encapsulated nitric oxide synthase is temperature-sensitive liposome encapsulated nitric oxide synthase which is released by local heat (this may be counterproductive in this on other embodiments where $O_2^-$ injury is being treated, but is useful in embodiments hereinafter where $O_2^-$ is being used to kill cells). Drugs not containing NO can be converted to contain NO as described in Stamler, et al. U.S. Application Ser. No. 08/852,490, the whole of which is incorporated herein by reference. Dosages for NO providing compounds are those suitable to provide from 1 ng to 10 mg NO. The dosages should be such as to replace NO normally present in the paraquat injured tissue which is NO depleted to restore the protective effect provided by NO and to scavenge $O_2^-$ which has been generated. The route of administration for the compounds is, for example, intravenous or inhaled or topical or liposome encapsulated. For DETA NONOate, the dosage range is preferably 1 nM to 10 mM and the route of administration is preferably intravenous. For NO-substituted tetracycline, the dosage range is preferably 1 ng to 1 mg and the route of administration is preferably intravenous. For NO-substituted cyclosporine, the dosage range is preferably 1 ng to 10 mg and the route of administration is preferably intravenous. For N-acetycysteine, a dosage range of 50 to 200 mg/kg is preferred. Adminstration is continued as long as improvement occurs.

We turn now to the third embodiment which is directed to a method for treating a patient having a disease in which nitric oxide synthase contributes to reactive oxygen production which causes tissue injury, comprising administering to said patient a therapeutically effective amount (i.e., a tissue injury attenuating effective amount) of nitric oxide synthase inhibitor that blocks electron transfer reactions of nitric oxide synthase, and of NO providing compound. Besides paraquat-induced injury, stroke is a disorder treated in this embodiment. Other disorders covered by this embodiment are, for example, adult respiratory distress syndrome (ARDS), pulmonary hypertension, atherosclerosis, transplant rejection, sepsis and complications resuing from treatment with L-NMMA or cyclosporine, e.g., pulmonary hypertension and accelerated atherosclerosis. The nitric oxide synthase inhibitors and dosages thereof and routes of administration include those the same as for the first embodiment, and the NO providing compounds, and the dosages thereof and routes of administration, are the same as those described for the second embodiment, including DETA NONOate, NO-substituted tetracycline and NO-substituted cyclosporine as compounds administered and the dosages and routes of administration described for them in the description of the second embodiment. In addition, a single compound can serve as both nitric oxide synthase inhibitor that blocks electron transfer reactions of nitric oxide synthase and as NO providing compound. Exemplary of such compound is NO-derivatized L-NAME. Various NO-derivatized L-NAME compounds and analogs thereof have the formula set forth below

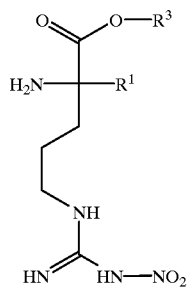

(I)

where $R^1$ is any of —$(CH_2)_x$—SNO, —$(CH_2)_x$—ONO, —$(CH_2)_x$—$ONO_2$, or —$(CH_2)_x$—$N(R^2)$—$NO^-$—$N=O$ where x is 1 to 4 and $R^2$ is alkyl, cycloalkyl, aryl or alkylaryl of 1–12 carbon atoms and $R^3$ is alkyl preferably methyl ethyl, propyl or isopropyl or where $R^1$ is H and $R^3$ is —$(CH_2)$—$C(CH_3)_2$—SNO, —$CH_2C(C_2H_5)_2$—SNO, or —$CH_2$—$(CHONO_2)_y$—$CH_2ONO_2$ where y is 0 to 6, or any of $R^1$ except H. The dosages and routes of administration for NO-derivatized L-NAME are the same as those for L-NAME described above in respect to the first embodiment. In another embodiment, the —$NO_2$ of compounds of formula (I) is replaced by —NO and $R^1$ and $R^3$ are the same as for the formula (I) compounds with —$NO_2$; the dosages and routes of administration can be the same as for the corresponding —$NO_2$ containing compounds. Various NO-derivatized L-thiocitrulline methyl ester compounds have the formula set forth below

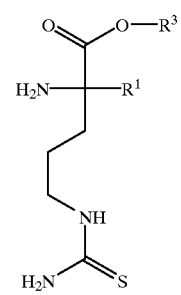

(II)

where $R^1$ and $R^3$ are as described for NO-derivatized L-NAME and analogs thereof The dosages and routes of administration for NO-derivatized L-thiocitrullne methyl ester are the same as those for L-thiocitrulline methyl ester described for the first embodiment. Various NO-derivatized L-nitroarginines have the formula

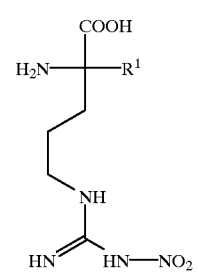

(III)

where $R^1$ is —$(CH_2)_x$—SNO, —$(CH_2)_x$—ONO, —$CH_2)_x$—$ONO_2$, or —$(CH_2)_x$—$N(R^2)$—$NO^-$—$N=O$, where x is 1 to 4 and $R^2$ is alkyl, cycloalkyl, aryl or alkylaryl of 1–12 carbon atoms. The dosages and routes of administration for NO-derivatized L-nitroarginine are the same as those for L-nitroarginine described for the first embodiment. Various NO-derivatized L-thiocitrullines have the formula

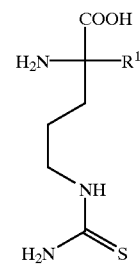

(IV)

where $R^1$ is the same as for NO-derivatized L-nitroarginine. The dosages and routes of administration for NO-derivatized L-thiocitrulline are the same as those for L-thiocitrulline described for the first embodiment.

We turn now to making of the compounds of formulas (I) and (III) where x in the descriptions of $R^1$ is 2.

We turn firstly to making of compound of formula (III). A multi-step synthesis is carried out as follows: Ethyl acetoacetate is alkylated sequentially on its β-carbon using first 2-bromoethanol and then acrylonitrile; all reagents are commercially available. The product is $CH_3COC(CH_2CH_2OH)(CH_2CH_2CN)CO_2Et$. That product is reacted with hydrazoic acid to form $CH_3CONHC(CH_2CH_2OH)(CH_2CH_2CN)CO_2Et$, and that product is then reduced with hydrogen over Pt to yield $CH_3CONHC(CH_2CH_2OH)(CH_2CH_2CH_2NH_2)CO_2Et$. That derivative is reacted with S-methyl-isothiourea to form $CH_3CONHC(CH_2CH_2OH)(CH_2CH_2CH_2NH-C(=NH)-NH_2)CO_2Et$. Acid hydrolysis of the N-acetyl group and the ethyl ester yields α-(2-hydroxyethyl)-DL-arginine. That is converted to the $N^\omega$-nitro derivative by treating with ice cold fuming nitric and sulfuric acids, the same procedure that is frequently used to convert L-arginine to $N^\omega$-nitro-L-arginine. After product isolation, a brief treatment with aqueous acid removes any nitrite or nitrate esters formed on the hydroxyl group. At this point the product, which is $N^\omega$-nitro-α-(2-hydroxyethyl)-DL-arginine, can be resolved into its D- and L-enantiomers by high-pressure liquid chromatography (HPLC) on chiral supports or on conventional supports using chiral solvents; these and other methods for chromatographically resolving racemic amino acid mixtures are well known in the art. $N^\omega$-nitro-α-(2-hydroxyethyl)-DL-arginine or $N^\omega$-nitro-α-(2-hydroxyethyl)-L-arginine can be nitrated or nitrosated on the free hydroxyl to yield compound of formula (III) in which $R^1$ is —$(CH_2)_2$—$ONO_2$ or —$(CH_2)_2ONO$, respectively, using standard procedures for making nitrate or nitrite esters. To convert to the α-(2-mercaptoethyl) or α-(2-alkylaminoethyl) derivatives, the α-amino group is first protected using carbobenzoxy chloride to form the CBZ-derivative, and the hydroxyl group is then activated by reaction with mesyl chloride. The product is $N^\alpha$-CBZ-$N^\omega$-nitro-α-($CH_2CH_2OSO_2CH_3$)-DL-arginine, which can be reacted with thiourea to form, after hydrolysis, the mercapto derivative or with an alkylamine to form the precursor of compound of formula (III) where $R^1$ is —$(CH_2)_2$—$N(R^2)$—$NO^-$—$N=O$ and $R^2$ is the alkyl group of the alkylamine. The CBZ group is removed by acid hydrolysis for the mercapto compound and by acid hydrolysis or hydrogenation for the secondary amino compound. The mercapto group is then S-nitrosated using sodium nitrite in HCl to form compound of formula (III) where $R^1$ is —$(CH_2)_2$—SNO. The secondary amino compound is converted to the NONOate using NO gas at 5 atm; the product is compound of formula (III) where $R^1$ is —$(CH_2)_2$—$N(R^2)$—$NO^-$—$N=O$.

We turn now to the making of the compounds of formula (I) where $R^1$ is —$(CH_2)_2ONO$ or —$(CH_2)_2ONO_2$. The starting point is the $N^\omega$-nitro-α-(2-hydroxyethyl)-L-arginine synthesized above. This is converted to the tert-butyloxycarbonyl derivative of the α-amino group, where tert-butyloxycarbonyl is the BOC protecting group, and the desired ester group is then formed by dissolving in the appropriate alcohol (methyl ethyl propyl or isopropyl), and adding dicyclohexylcarbodiimide. Then deprotection is carried out using non-aqueous acid (e.g., trifluoroacetic acid), and the resulting derivatives are converted to nitrite or nitrate esters using standard procedures. Compounds of formula (I) where $R^1$ is —$(CH_2)SNO$ and —$(CH_2)_2N(R^2)$—$NO^-$—$N=O$ where $R^2$ is alkyl cycloalkyl aryl or alkylaryl of 1–12 carbon atoms are prepared similarly from corresponding alcohols, mercaptans and amines except that in addition to using BOC to protect the α-amino group, BOC is used to protect the secondary amino function and trityl is used to protect the thiol group.

We turn now the fourth embodiment that is directed to a method for treating a patient having a disease where treatment with nitric oxide synthase inhibitor ameliorates symptoms of the disease but lowers the NO level to a cytotoxic level or where it is beneficial to supplement nitric oxide synthase inhibitor treatment with treatment with NO providing compound, comprising administering to said patient the nitric oxide synthase inhibitor in the therapeutically effective amount and a therapeutically effective amount (an amount to restore NO level to a non-cytotoxic or benefit providing level) of NO providing compound. The diseases include, for example, sepsis, stroke, cystic fibrosis and adult respiratory distress syndrome. Examples of nitric oxide synthase inhibitors, dosages therefor and routes of administration for sepsis include LNMMA (dosage range 0.4 mg/kg to 100 mg/kg, route of administration: intravenous, preferably a bolus intravenous loading dose of 1 to 20 mg/kg followed by infusion of 10 mg/kg/hr.), L-NAME (e.g., dosage, for example, of 0.1 mg/kg, route of administration: intravenous), imidazoles (dosage 0.01 to 100 mg/kg, route of administration: intravenous), and BN 80933; for stroke include L-NMMA (dosage, e.g., 1 to 20 mg/kg, route of administration: intravenous) and imidazoles (dosage 0.01 to 100 mg/kg, route of administration: intravenous); and for adult respiratory distress syndrome (ARDS) include L-NMMA (dosage of 0.1 mg/kg to 100 mg/kg and route of administration is inhaled or intravenous), and L-NAME (dosage of 0.05 mg/kg–0.4 mg/kg and route of administration is inhaled or intravenous). NO providing compounds and dosages therefor and routes of administration are the same for these compounds as described for the second embodiment including DETA NONOate, NO-substituted tetracycline and NO-substituted cyclosporine as compounds administered and the dosages and routes of administration described for them in the description of the second embodiment. Since tetracycline and cyclosporine are nitric oxide synthase inhibitors, the NO-substituted tetracycline and NO-substituted cyclosporine serve as both the nitric oxide synthase inhibitor and NO providing compound as in the third embodiment. NO-substituted nitric oxide synthase inhibitors including those described for the second and third embodiments and the dosages and routes of administration associated therewith are useful as single treating agents in this embodiment to serve both as the nitric oxide synthase inhibitor and also as the NO providing compound. NO-derivatized L-NAME is a preferred agent to provide both nitric oxide synthase inhibitor and NO providing compound; the dosages and routes of administration are the same as those described for the third embodiment.

We turn now to the fifth embodiment of the invention, which is directed to a method of treating a patient with a disease characterized by pathologically proliferating cells containing nitric oxide synthase, comprising administering to said patient a therapeutically effective amount (i.e., a pathologically proliferating cell killing effective amount) of a dipyridinum compound and wherein in one alternative agent that induces expression of nitric oxide synthase is also administered. The pathologically proliferating cells in one case are those of high grade tumors (i.e., tumors that are resistant to conventional therapeutic agents), e.g., in Kaposi's sarcoma, breast cancer, melanoma, lung cancer, squamous cell carcinomas including carcinomas of the head and neck and adenocarcinoma, leukemic cells and solid tumors. Other cases of pathologically proliferating cells are restenosis, benign prostatic hypertrophy and pulmonary hypertension. The agents that induce nitric oxide synthase include agents that genetically alter the pathologically proliferating cells (e.g., transgenes or viral vectors containing DNA that expresses nitric oxide synthase (NOS)), liposomes containing NOS, paraquat, cytokines, tamoxifen, HMG CoA reductase inhibitors and estrogen (to stimulate overexpression of NOS). The induction of nitric oxide synthase is preferably carried out prior to administration of the dipyridinum compounds when the agent relied on to induce nitric oxide synthase is not paraquat or is used in addition to paraquat. Paraquat can be used both to induce nitric oxide synthase and as a dipyridinium compound. Suitable cytokines include interferons, tumor necrosis factor, and interleukins. The same dosages and routes of administration used for cytokines for other disorders are useful here. In general, dosages for cytokines range from 1 ng to 100 mg. The dosage for tamoxifen is $10^{-7}$ to $10^{-4}$ M and the route of administration is oral. The HMG CoA reductase inhibitors and dosages and route of administration of these used for cholesterol blood level reduction are useful here. In general, the dosage range and routes of administration for the dipyridinum compounds are 1 ng to 1 gm, but may be higher when administered locally. One dipyridinum compound is paraquat, and the dosages and routes of administration are 1 ng to 100 mg, for example, 5 to 200 $\mu$M or 0.1 to 5 mg/kg and route of administration is, for example, topical, local, intravenous, via liposome or inhaled. Other dipyridinum compounds, are pyridinium compounds that are reduced by nitric oxide synthase and include for example, diquat and lucigenin, and the dosages and routes of administration are similar to those for paraquat. In one case, the dipyridinum compound does not have an acylamino sub stituent.

We turn now to the sixth embodiment of the invention, which is directed to a method of treating a patient affected with a disorder in which reactive oxygen species contribute to the pathology, comprising administering to said patient a therapeutically effective amount of a nitric oxide synthase inhibitor which blocks generation of reactive oxygen species from NOS. As indicated above, this embodiment is generic to the first embodiment. Besides paraquat-induced injury (the first embodiment) the disorders include stroke and adriamycin toxicity. The nitric oxide synthase inhibitors, dosages and routes of administration therefor are the same as those described in conjunction with the first embodiment and the third embodiment. In various cases, the nitric oxide synthase inhibitor is not L-NAME or is L-NAME used after administration of L-NMMA is not sufficiently effective or is an NO-derivatized LNAME.

We turn now to the seventh embodiment of the invention, which is directed to a method of inhibiting nitric oxide synthase in a patient in need thereof comprising administering to said patient a therapeutic amount (ie., a nitric oxide synthase inhibiting effective amount) of agent with a redox potential greater than nitric oxide synthase and an $LD_{50}$ greater than 1 $\mu$M or 100 times the effective dose for systemic non-liposome or other non-local administration, to inhibit nitric oxide synthase, and optionally to provide therapeutic effect except required in those cases to provide novelty a therapeutic amount of NO providing compound. The patients in need of nitric oxide synthase inhibition include those with the following disorders: sepsis, hypotension, inflammatory disorders, asthma, pathologically proliferating cells containing nitric oxide synthase (e.g., tumors containing nitric oxide synthase, proliferating cells of restenosis, proliferating cells of benign prostatic hypertrophy, proliferating cells of pulmonary hypertension and the pathologically proliferating cells of an infective organism), rejection, autoimmune disease, neurodegeneration, and other chronic degenerative diseases. The agents with redox potential greater than that of nitric oxide synthase include paraquat; methylene blue, ellipticinium, acridine, phenazine, adriamycin, quinones, diquat, lucigenin, Azure A, Azure B, Azure C, pyocyanin, acriflavine, lynasine, phenacridine, aminochromes, palmatine, and homiclium (also known as ethidium). The dosages and routes of administration for paraquat are those given above in the fifth embodiment. The dosages for the other listed compounds can be 1/100 of the $LD_{50}$ and the routes of administration are the same as those where the compounds are administered for other conditions. The NO providing compounds and dosages and routes of administration associated therewith can be the same as those described above in conjunction with the second embodiment.

We turn now to the eighth embodiment of the invention which is the seventh embodiment where the patient is affected with a disorder characterized by pathologically proliferating cells containing nitric oxide synthase and the agent in inhibiting nitric oxide synthase accepts electrons from it to generate reactive oxygen to kill the pathologically proliferating cells. The disorders include tumors, especially high grade tumors (e.g., from one of the following kinds of cancer in Kaposi's sarcoma, breast cancer, melanoma, lung cancer, squamous cells carcinomas including carcinomas of the head and neck and adenocarcinoma, leukemic cells and solid tumors), restenosis, benign prostatic hypertrophy, pulmonary hypertension, and infection (in bacterial, fungal and parasitic infections the proliferating pathogenic cells contain nitric oxide synthase and in viral infections the virus can induce nitric oxide synthase within the infected cell). The agents include methylene blue, ellipticinium, acridine, phenazine, adriamycin and quinones; the dosage ranges and routes of administration recited above for these agents for the seventh embodiment are the same for the eighth embodiment. The NO providing compounds and dosages and routes of administration associated therewith can be the same as those described above in conjunction with the second embodiment.

We turn now to the ninth embodiment of the invention, which is directed to a method of treating a patient affected with pathologically proliferating cells containing a diaphorase or affected with a disease producing a diaphorase (e.g., cystic fibrosis), comprising administering to said patient a therapeutically effective amount (i.e., a pathologically proliferating cell killing effective amount) of agent with a redox potential greater than the diaphorase and an $LD_{50}$ greater than 1 $\mu$M or 100 times the effective dose for systemic non-liposome or other non-local administration to generate reactive oxygen and kill the pathologically proliferating cells, and optionally to provide therapeutic effect except required in those cases where necessary to provide novelty therapeutic amount of NO providing compound. As indicated above, this embodiment is generic to the eighth embodiment. The term "diaphorase" is used herein to mean enzyme that gives up electrons to the agent to produce reduced agent that reduces oxygen thereby generating $O_2^-$ or $H_2O_2$. Besides NOS, the diaphorases include, for example, cytochrome P450 enzymes, e.g., cytochrome P450 reductase, other cytochromes, mono- or dioxygenases, peroxidases, flavoproteins and globins including flavohemoglobin, GSSG reductase and DT diaphorase. The pathologically proliferating cells include tumor cells (e.g., high grade tumors) from cancers as described above, restenosis, benign prostatic hypertrophy, proliferating cells in pulmonary hypertension and pathogen cells in infections. The agents include, for example, methylene blue, ellipticinium, acridine, phenazine, adriamycin, quinones, diquat, dipyridinium compounds including paraquat, lucigenin, Azure A, Azure B, Azure C, pyocyanin, acriflavine, lynasine, phenacridine, aminochromes, palmatine and homiclium. The dosages and routes of administration recited for these compounds for the seventh embodiment are the same for the ninth embodiment. The NO providing compounds and dosages and routes of administration thereof can be the same as those described above in conjunction with the second embodiment.

We turn now to the tenth embodiment of the invention, which is directed to a method of treating a patient affected with pathologically proliferating cells, comprising causing overexpression of nitric oxide synthase in said patient and then administering to said patient a therapeutic amount (ie., a pathologically proliferating cell killing effective amount) of agent with redox potential greater than nitric oxide synthase and an $LD_{50}$ greater than 1 $\mu$M or 100 times the effective dose for systemic non-liposome or other non-local administration. This embodiment is generic to the case of the fifth embodiment where agent inducing expression of nitric oxide synthase is administered and also a therapeutically effective amount of dipyridine compound is administered to treat a patient affected with pathologically proliferating cells including where dipyridine compound serves both to induce nitric oxide synthase and to kill pathologically proliferating cells. The pathologically proliferating cells can be tumors as described above from cancers as described above, restenosis, benign prostatic hypertrophy, proliferating cells of pulnonary hypertension and the cells of infection causing pathogens. The overexpression of nitric oxide synthase can be caused in the same ways as in the case of the fifth embodiment of the invention where this is carried out. The agents, dosages therefor and routes of administration can be the same as those discussed for the seventh embodiment.

We turn now to the eleventh embodiment of the invention, which is directed to a method of treating a patient in need of constricting of blood vessels, said method comprising administrating to said patient a therapeutically effective amount (ie., a blood vessel constricting effective amount) of agent with redox potential greater than nitric oxide synthase and an $LD_{50}$ greater than 1 $\mu$M or 100 times the effective dose for systemic non-liposome or other non-local administration, and optionally to provide therapeutic effect except required in those cases where necessary for novelty, a therapeutic amount of NO providing compound. The disorders where a patient needs constricting of blood vessels include hypotension (to increase blood pressure), tumors (to starve the tumor), to prevent reperfusion injury (e.g., in accident victims) or to close off a ductus arteriosus or to prevent bleeding or to close off other unwanted vessels (e.g., retinopathy or skin lesions). The agents, dosages and routes of administration can be the same as those for the seventh embodiment. In one case, the agent is a dipyridinium compound which does not have an acylamino substituent, e.g., paraquat, with the dosages and routes of administration described above in association with these. The NO providing compounds and dosages and routes of administration therefor are the same as those described for the second embodiment.

We turn now to the twelfth embodiment of the invention which is directed to treating patients for disorders where generation of $O_2^-$ or product thereof provides benefit, comprising administering to said patient an amount of agent with a redox potential greater than nitric oxide synthase and an $LD_{50}$ greater than 1 $\mu$M or 100 times the effective dose for systemic non-liposome or other non-local administration to generate $O_2^-$ from nitric oxide synthase or other agent which generates $O_2^-$ from nitric oxide synthase in the patient, and optionally to provide therapeutic effect except required in those cases for providing novelty therapeutic amount of NO providing compound. As indicated above, this embodiment is generic to all or a portion of the fifth embodiment, the eighth embodiment and the ninth embodiment. Besides the appropriate disorders in those embodiments, another disorder treated in this embodiment is heart failure; the $O_2^-$ increases force production in the heart and skeletal muscle and therefore is a treatment for heart failure. Still other disorders covered by this embodiment are skeletal muscle weakness or those disorders ameliorated by induction of growth differentiation thereby causing tissue to regenerate, e.g., in wound healing or angiogenesis. The agents with redox potential and $LD_{50}$ specified described above, and dosages and routes of administration associated therewith, are the same as those described for the firth, eighth and ninth embodiments. The other agents which generate $O_2^-$ include nitric oxide synthase inhibitors which do not block electron transfer reactions of nitric oxide synthase, including L-NMMA; the dosages and routes of administration can be the same as those described above for L-NMMA. The NO providing compounds and dosages and routes of administration associated therewith are the same as those described in conjunction with the second embodiment.

Description in relation to the seventh, eighth, ninth, eleventh and twelfth embodiments states "except where required in those cases where necessary for novelty." This means that one or more agents with redox potential greater than nitric oxide may have been used before to treat the disorders before the invention herein, and in such case the agent is administered together with an NO providing compound or is NO-substituted to distinguish the prior art and provide additional benefit. This may be the case, for example, where the agent with redox potential greater than nitric oxide synthase is ellipticinium or acridine or methylene blue or phenazine or adriamycin or a quinone.

The invention is explained and illustrated by the following background examples and working examples. In the examples the NO-derivatized LNAME is the compound of formula (I) where $R^3$ is $CH_3$ and $R^1$ is —$(CH_2)_2$—$ONO_2$. This compound is made by starting with $N^{\omega}$-nitro-$\alpha$-(2-hydroxyethyl)-L-arginine made as described above, forming the tert-butyloxycarbonyl derivative, dissolving in methanol, adding dicyclocarbodiimide, using non-aqueous trifluoroacetic acid to remove the protecting group and converting to the nitrate ester. Therapeutic results are also obtained when the NO-derivatized L-NAME is the compound of formula (I) where $R^3$ is $CH_3$ and $R^1$ is —$(CH_2)_2$—ONO.

BACKGROUND EXAMPLE 1

Recombinant rat neuronal nitric oxide synthase (NOS1, Oxis, Portland, Oreg.), a constitutive enzyme, was used to assay NADPH oxidation in the presence of increasing concentrations of paraquat. Reactions (0.2 ml) were performed in bis-tris propane buffer (40 mM) containing L-arginine (1 mM), $CaCl_2$ (1.2 mM), EDTA (0.9 mM), NADPH (0.35 mM), dithiothreitol (3 mM), tetrahydrobiopterin (4 $\mu$M), catalase (1 $\mu$g/ml) and calmodulin (200 U/ml) at pH 7.4. Reactions were initiated by the addition of 1.5 U of NOS1, and the oxidation of NADPH was continuously monitored at 340 nm for 1 minute at 37° C. in a plate reader.

The rate of NOS-mediated NADPH oxidation was determined using an extinction coefficient of 6.22 mM$^{-1}$ cm$^{-1}$ after subtracting the baseline of NADPH oxidation. The results are shown in FIG. 1(a). As shown in FIG. 1(a), the addition of paraquat to recombinant NOS1 reaction mixture produced a concentration-dependent increase in NADPH oxidation.

Figure 1B:
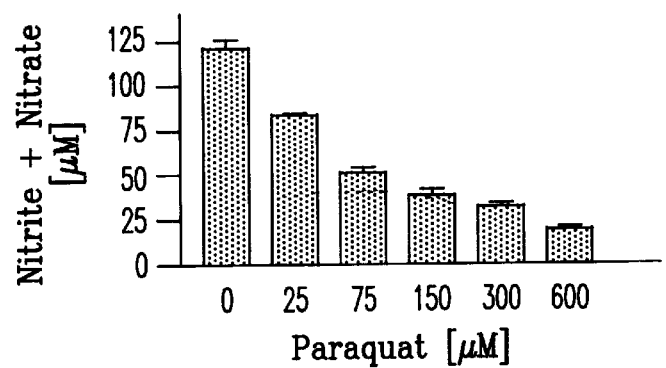
FIG. 1(b) is a graph of paraquat concentration versus total nitrite and nitrate and shows results of Background Example 1.

The same microtiter plates used above were left at room temperature for 5 hours and then an aliquot was assayed for total nitrite and nitrate. Nitrite and nitrate were assayed using a non-enzymatic colorimetric kit (NB-88, Oxford Biomedical Research, Oxford, Mich.). NADPH oxidation was stopped after 5 hours by addition of 25 μl of zinc sulfate (30% w/v) to precipitate the NOS protein. Nitrate was non-enzymatically converted to nitrite by overnight incubation of 150 μl of reaction mixture from the NADPH oxidation assay with cadmium beads. Nitrite concentration was determined from a standard curve using 100 μl sample or standard. The results are shown in FIG. 1(b). As shown FIG. 1(b), the formation of NO was inhibited by paraquat. (There was a concentration dependent decrease in NO formation as assessed by accumulation of nitrite and nitrate.) Thus, the formation of NO was inversely related to diaphorase (oxidation) activity. The calculated concentration of paraquat that inhibited NO formation by 50% ($IC_{50}$) was 62 μM with a 95% confidence level of 47–82 μM. NOS1 was found to exhibit paraquat diaphorase activity even in the presence of 1 mM L-arginine.

Figure 1C:
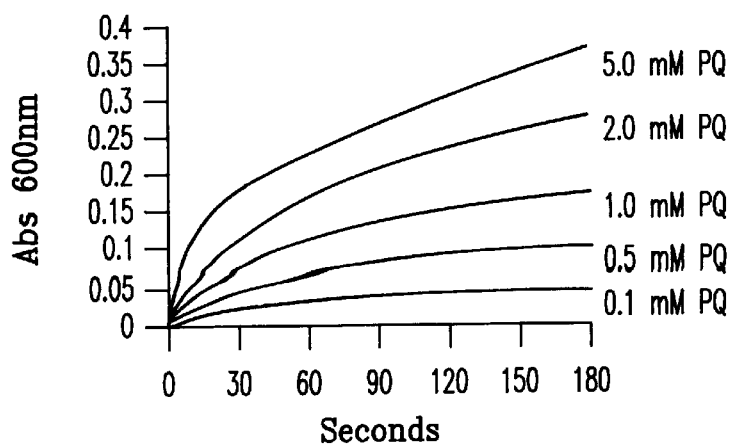
FIG. 1(c) is a graph of time versus anaerobic reduction of paraquat in terms of spectrophotometric analysis at 600 nm and shows results of Background Example 1.
Figure 1D:
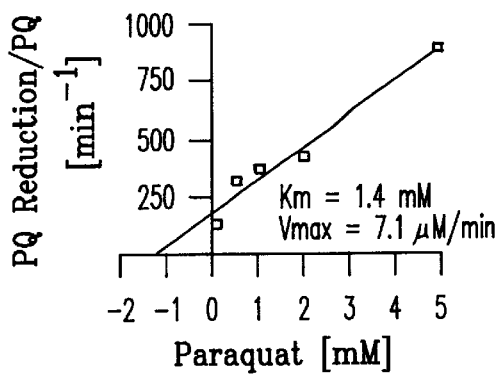
FIG. 1(d) is a Hanes plot for paraquat reductase activity of rat NOS1 and shows results of Background Example 1.

Anaerobic reduction of paraquat by NOS1 to paraquat.$^+$ was followed at 600 nm spectrophotometrically and converted to a concentration using the extinction coefficient $E_{600}$=13,700 M$^{-1}$ cm$^{-1}$. Reactions (1 ml) were performed in the NADPH oxidation buffer described above in the absence of L-arginine, dithiothreitol and tetrahydrobiopterin. Reactions were initiated by the addition of 2 U of NOS1 and followed for 3 minutes at 37° C. The results are shown in FIG. 1(c). The results confirm the direct and progressive reduction of paraquat to its cation radical under anaerobic conditions as evidenced by the increasing intensity at 600 nm A Hanes plot ($K_m$ and $V_{max}$ values) for paraquat reductase activity of rat NOS1 is shown in FIG. 1(d). The results show increased paraquat reduction with increasing paraquat concentration.

The results show that paraquat inhibits NOS activity and that paraquat is an NOS diaphorase and causes superoxide formation.

BACKGROUND EXAMPLE 2

Figure 2A:
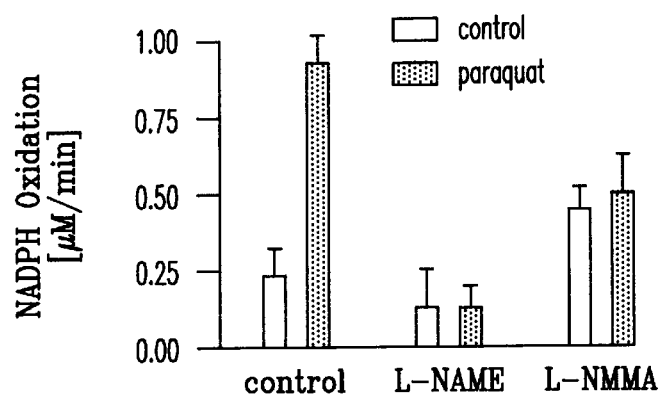
FIG. 2(a) is a graph of the effect of L-nitroarginine, methyl ester (L-NAME) and L-N-methylargine (L-NMMA) on NAPDH oxidation in the presence or absence of paraquat and shows results of Background Example 2.

The experiment of Background Example 1 for NADPH oxidation was carried out in the presence and absence of 25 μM paraquat, without any NOS inhibitor (control), in the presence of L-NAME (1 mM) or in the presence of 1 mM L-NMMA. The paraquat without NOS inhibitor increased NAPDH oxidation about three-fold over the basal rate. L-NAME (mM) had little effect on basal NADPH oxidation but completely inhibited paraquat-stimulated NADPH oxidation. L-NMMA (1 mM) produced a small increase in basal NADPH oxidation and partially blocked paraquat-induced NADPH oxidation. The NOS inhibitors thus exhibited differential effects on NOS1's ability to act as a paraquat diaphorase. Only L-NAME shut down the NADPH oxidase activity. Results are shown in FIG. 2(a).

To test whether the above effect was present in intact cells, endothelial cell cultures, constitutively expressing NOS3 protein as determined by western blot analysis, were treated with 2 mM paraquat in the presence of increasing concentrations of either L-NAME or L-NMMA.

The endothelial cells were obtained as follows: CPA-47 endothelial cell line (CRL-1733) was purchased from American Type Culture Collection (Manassas, Va.). Endothelial cells were grown in T-75 flasks containing Ham's F-12 K medium supplemented by 1 mM L-glutamate and 10% equine serum (Gibco-BRL, Grand Island, N.Y.). Endothelial cells were plated at 3.5×10$^4$ cells/well in 24-well plates and experiments were performed 48 hours later when cells were near confluence. Medium was changed to minimal essential medium without serum supplement. Endothelial cells were from passages 30–36.

Western blot analysis was carried out as follows. Cells were lysed in ice-cold 50 mM Tris buffer (pH 7.4) containing 1% sodium dodecyl sulfate and protease inhibitor cocktail (Boehringer Mannheim). Protein (10 μg) was separated on a 4–20% gradient SDS-PAGE at 250 V for 30 minutes and transferred onto a nitrocellulase membrane at 30 V for 12 hours. Proteins were detected using polyclonal antibodies against human NOS3 (Transduction Laboratories; 1/1000) and nitrated keyhole limpet hemocyanin, nitrotyrosine (Upstate Biology; 1/5000). Primary antibodies were detected with a goat anti-rabbit-HRP antibody (Jackson; 1/15,000) and developed using an ECL kit (Amersham).

Cytotoxicity was measured as the percent release of LDH and compared to vehicl-treated cells (basal). The percent release of cytosolic lactate dehydrogenase (LDH) into the culture medium was used to assess the integrity of the cell membrane. LDH activity was measured by following the loss of NADH at 340 nm as described in Day, B. J., et al., J. Pharmacol. Exp. Ther. 275, 1227–1232 (1995). The percent release of LDH into the culture medium 24 hours after the paraquat treatment was used to assess cell injury.

Figure 2B:
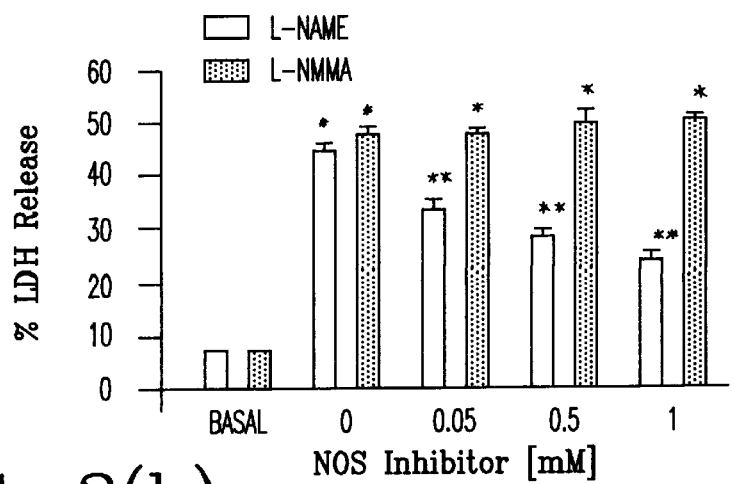
FIG. 2(b) is a graph of effect of L-NAME and L-NMMA on percent lactate dehydrogenase (LDH) release in the presence of paraquat and shows results of Background Example 2.

The results are shown in FIG. 2(b) where a single asterisk indicates a significant difference from the control group, and double asterisk indicate a significant difference from the paraquat group, p<0.05. As shown in FIG. 2(b), paraquat produced a three-fold increase in LDH release. L-NAME, but not L-NMMA, produced a dose-dependent protection from paraquat toxicity. These data are consistent with the differential effect of the two inhibitors on the NADPH oxidase activity of NOS and suggest that part of the toxicity exerted by paraquat in endothelial cells is due to NOS3 acting as a paraquat diaphorase. The data shows that paraquat-induced endothelial cell toxicity is attenuated by inhibitors of NOS that prevent NADPH oxidation but is not attenuated by those that do not.

BACKGROUND EXAMPLE 3

Rabbit aortic rings were treated with increasing concentrations of paraquat or L-NAME (2 mM) prior to initiating a constriction response with 1 μM phenylephrine (initial contraction).

New Zealand white male rabbits weighting 3–4 kg were anaesthetized with phenobarbital (30 mg/kg/iv). The descending thoracic aorta was isolated and placed in Krebs-Henseleit buffer (pH 7.4) and stored at 4° C. until used. The vessels were cut into 5 mm rings and submerged in 25 ml double jacketed tissue baths containing Krebs-Henseleit buffer bubbled with 95% oxygen and 5% carbon dioxide at 37° C. Rings were hung on stainless steel stirrups connected to calibrated force transducers. Rings were equilibrated with 2 g resting tension for 1 hour before use and contracted with phenylephrine (1 μM). Rings were incubated with paraquat for 15 minutes before acetylcholine-induced or exogenous relaxations were performed.

Endothelial-derived relaxing factor (EDRF) responses were initiated by addition of acetylcholine.

Figure 3A:
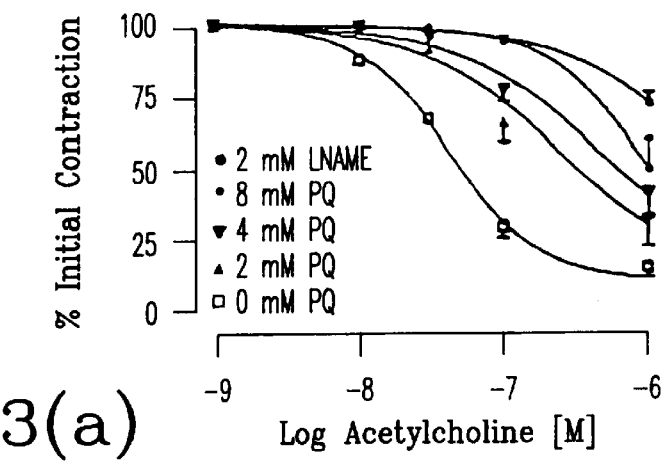
FIG. 3(a) is a graph of log acetylcholine concentration versus percent initial contraction in the presence of L-nitroarginine methyl ester (L-NAME) or in the presence of no paraquat or increasing concentrations of paraquat and shows results of Background Example 3.

The results are shown in FIG. 3(a). As shown in FIG. 3(a), paraquat produced a dose-dependent inhibition of EDRF-induced relaxation and greater than 90% of the relaxation response in this bioassay was inhibited by L-NAME.

In another case, rabbit aortic rings were constricted with 1 μM phenylephrine (initial contraction) and relaxed with increasing concentration of NO in the presence or absence of 2 mM paraquat. The results are shown in FIG. 3(b) where relaxations are expressed as a percent of the initial phenylephrine-induced contraction.

Figure 3B:
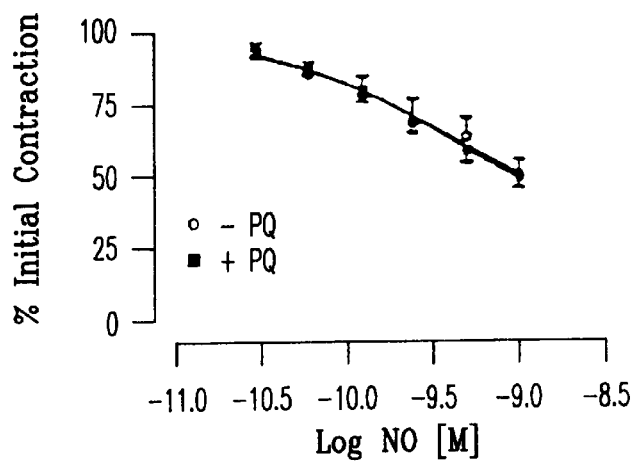
FIG. 3(b) is a graph of log NO concentration versus percent initial contraction in the presence or absence of paraquat and shows results of Background Example 3.

As shown in FIG. 3(b), paraquat did not inhibit exogenously added NO-induced relaxation. These data are consistent with NOS3 acting as a paraquat diaphorase at the expense of NO synthesis. These data show paraquat blocks EDRF responses and thereby constricts blood vessels. These data also show that paraquat can be used to block NOS without killing anything, just raising blood pressure (arterial tension). This data shows that NO still works in a system where NO is inhibited and superoxide is generated.

BACKGROUND EXAMPLE 4

The RAW-264.7 monocyte macrophage cells line (TIB-71) was purchased from the American Type Culture Collection (Manassas, Va.). The cells were grown in T-75 flasks containing DMEM (Gibco-BRL, Grand Island, N.Y.) supplemented with 1 mM pyruvate, 4.5 g/L glucose and 1,070 fetal bovine serum Macrophages were plated at 2.0× $10^4$ cells/well in 24-well plates and experiments were performed when cells were near confluence. Macrophages were immunostimulated with 50 ng/ml lipopolysaccharide (LPS) from *E. coli* serotype 0111:B4 (Signia, St. Louis, Mo.) and 50 U/ml recombinant mouse interferon gamma (INF-γ, R&D Systems, Minneapolis, Minn.). Macrophages were used between passages 2–8. Cell cultures were kept in a 37° C. incubator with air and 5% carbon dioxide.

NOS2 was induced in RAW cells using a mixture of interferon-γ and lipopolysaccharide (LPS) referred to as "cytomix." Unstimulated (basal) and activated (cytomix) macrophages were treated with 0.1 mM paraquat or not treated with paraquat and cytotoxicity and NO production were assessed at 24 hours.

Figure 4A:
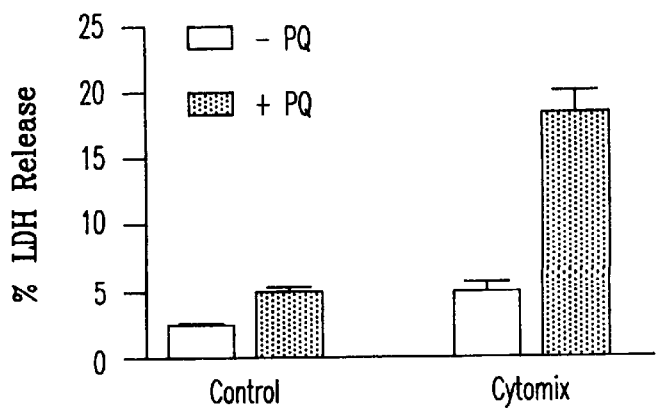
FIG. 4(a) is a graph of the effect of a mixture of interferon-γ and lipopolysaccharide (Cytomix) on percent LDH release in the presence or absence of paraquat from RAW cells and shows results of Background Example 4.

Cell injury was assessed by measuring LDH release. The results are shown in FIG. 4(a). As shown in FIG. 4(a), paraquat or cytormix treatments above produced very little cell injury. However, paraquat-induced cytotoxicity was potentiated in activated macrophages.

Figure 4B:
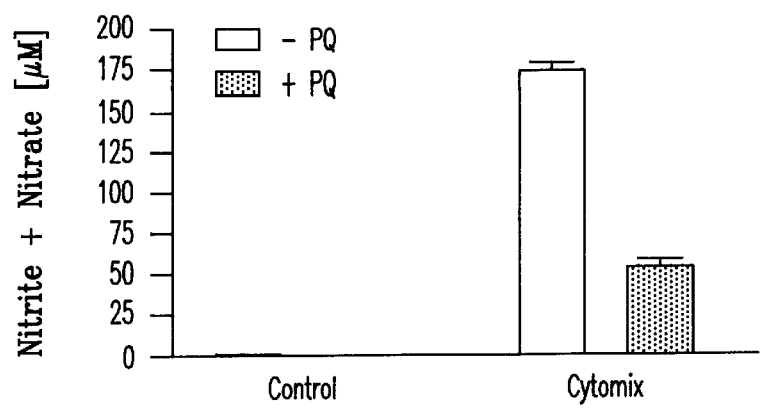
FIG. 4(b) is a graph of the effect of Cytomix on total nitrite plus nitrate production from RAW cells in the presence or absence of paraquat and shows results of Background Example 4.

NO production, assessed by measuring the accumulation of the NO metabolites nitrite and nitrate 24 hours after cytomix treatment, is shown in FIG. 4(b). As shown in FIG. 4(b), paraquat significantly attenuated NO production. NOS2 expression was not affected (data not shown). The inhibition of NO production could not be explained by increased cytotoxicity, since percent decrease in nitrite and nitrate was greater than percent increase in cell death. A decrease in nitrotyrosine staining was seen with the combination of paraquat and cytomix. These data are consistent with NOS2 in activated macrophages acting as a paraquat diaphorase and with cytotoxicity resulting from overproduction of $O_2^-$, not NO or peroxynitrate.

Figure 4C:
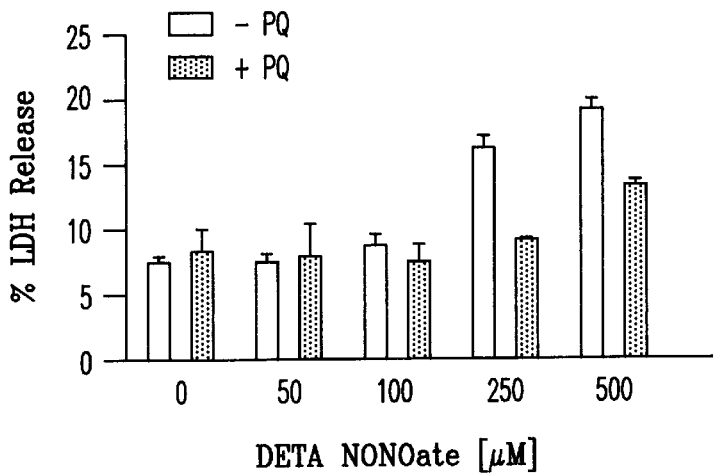
FIG. 4(c) is a graph of N,N-diethyl-3-methylbenzamide (DETA) NONOate concentration versus percent LDH release in the presence and absence of paraquat and shows results of Background Example 4.

To further exclude the role of peroxynitrite, macrophages were treated with increasing concentrations of the NO-donor, DETA NONOate in the presence of 0.1 mM paraquat. Macrophage cytotoxicity and NO release were assessed 24 hours after treatments. Cell injury was assessed by measuring LDH release. The results are shown in FIG. 4(c). As shown in FIG. 4(c), paraquat toxicity was not potentiated by DETA NONOate at concentrations that generated similar amounts of NO to those produced by activated macrophages. At higher concentrations, DETA NONOate-induced cell injury was attenuated by paraquat.

Figure 4D:
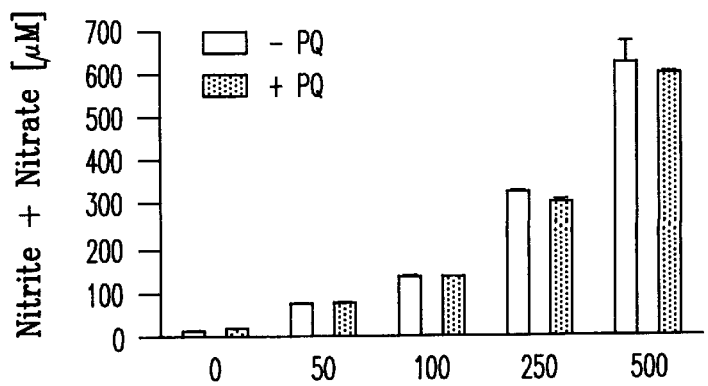
FIG. 4(d) is a graph of DETA NONOate concentration versus total nitrate plus nitrite concentration in the presence and absence of paraquat and shows results of Background Example 4.

The NO metabolite production is shown in FIG. 4(d). As shown in FIG. 4(d), paraquat does not alter the formation of NO metabolites from DETA NONOate.

Aconitase activity (a sensitive marker of $O_2^-$ and peroxynitrite formation) and fumarase activity were measured as described in Patel, M., et al., Nuron 16, 345–355 (1996). Specifically aconitase activity was determined spectrophotometrically by monitoring the formation of cis-aconitate from isocitrate at 240 nm. Fumarase activity was measured by monitoring the increased absorbence at 240 mn following the formation of fumarate from L-malate. Aconitase activity was expressed as a ratio of aconitase activity to flimarase activity in order to correct for differences in cell numbers.

Figure 5:
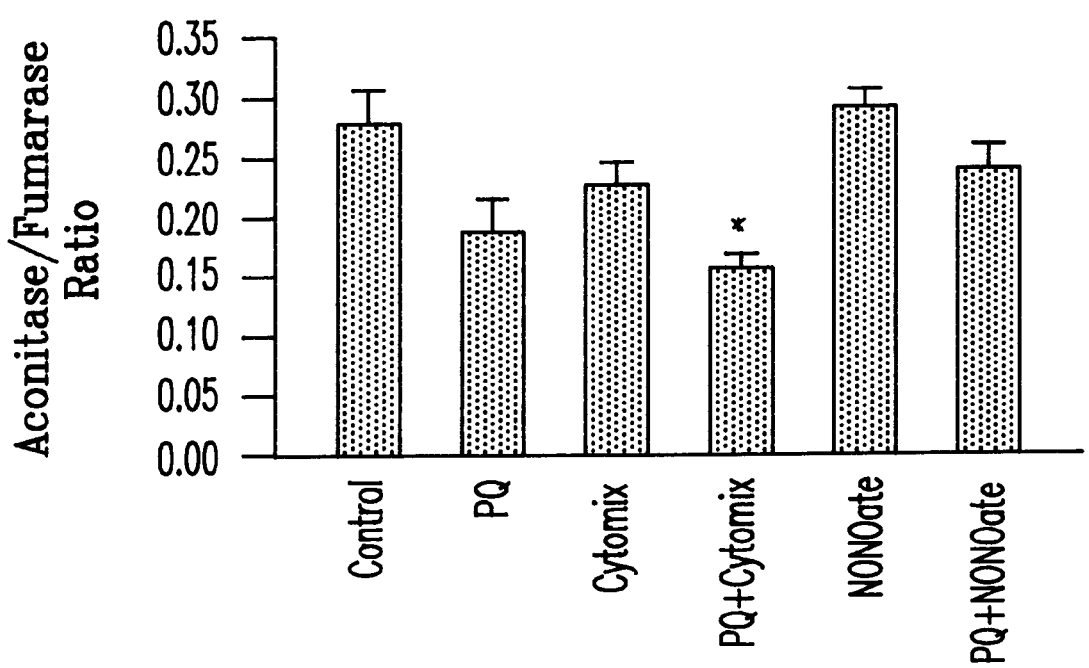
FIG. 5 is a graph of the effect of paraquat, Cytomix, NONOate and combinations thereof on aconitase/fumarase ratio (evidence of superoxide generation).

Aconitase activity was measured in cell lysates 24 hours after cytomix, DETA nonoate and paraquat treatments. Macrophages were grown in 24-well plates and treated with cytomix or 250 μM DETA NONOate. Control, activated (cytomix) and DETA NONOate groups were treated with paraquat (0.1 mM) or not treated with paraquat. The results are shown in FIG. 5 where an asterisk indicates a significant difference from control group, p<0.05. As shown in FIG. 5, a decrease in aconitase activity is seen in the paraquat (PQ)/cytomix group but not seen in the paraquat/DETA NONOate group. These results are consistent with those shown in FIGS. 4(c) and 4(d). Taken together the results show that potentiation of paraquat-induced cell injury in activated macrophages is not due to direct interaction between $O_2^-$ and NO.

These results show that paraquat-induced cytotoxicity is potentiated in cytokine-activated macrophages in a manner that correlates with its ability to block NO fornation and that toxicity can be ameliorated by putting NO back into the system indicating that the NO is restoring NO protection to cells and scavenging $O_2^-$. The results show paraquat kills cells containing NOS but not cells that do not.

SUMMARY FROM BACKGROUND EXAMPLES

Paraquat blocks neuronal, endothelial and macrophage NOS activity. Paraquat-induced endothelial cell toxicity is blocked by inhibitors of NOS that prevent NADPH oxidation, but is not attenuated by those that do not. Paraquat inhibits endothelium derived but not NO-induced relaxations. Paraquat toxicity in endothelial cells and macrophages correlates with its ability to produce $O_2^-$. Finally, paraquat induced cytoxicity in cytokine-activated macrophages correlates with its ability to block endogenous NO formation.

Working Example I

A 30-year-old white male presents complaining of shortness of breath after working with paraquat. A chest X-ray reveals changes compatible with pulmonary edema. An intravenous line is inserted and the patient is started on IV infusion of 0.1 mg per kilogram per minute L-NAME. His symptoms improve over the day, during which time his arteriolar $PO_2$ increases from 60 to 85 mm Hg. Over the following two days he is weaned off L-NAME.

Working Example II

A 40-year-old psychotic male attempts suicide by ingesting 1 gram of paraquat. He presents short of breath. His work-up reveals diffuse inertial changes on X-ray, pulmonary edema, a PO$_2$ of 60 mm Hg, and a creatinine of 4. The patient is given inhaled nitric oxide at 40 parts per million and started on 2 inches of nitropaste (nitroglycerin applied topically) every 4 hours.

Working Example III

A 70-year-old white male presents with confusion and weakness in the left arm. A CAT scan shows a right cortical stroke. He is begun on L-NAME (0.1 milligram per kilogram per minute IV); however, his symptoms do not improve and the course of therapy is complicated by a blood pressure of 220/110. The L-NAME is stopped and the patient is given an NO derivatized L-NAME compound at 0.1 milligram per kilogram per minute IV which lowers the blood pressure to 170/100. Over the following day the symptoms of confusion abate and motion returns to the arm.

Working Example IV

A 23-year-old white female with *E. Coli* bacteremia presents with a fever of 101° F. and a blood pressure of 70/50. She is administered a L-NMMA infusion at 10 mg/kg/hr. and develops profound pulmonary hypertension and a fall in cardiac output. The drug is stopped and she is begun on NO-derivatized L-NAME at 0.1 mg/kg/minute. Pulmonary pressure normalizes. Cardiac output normalizes. Blood pressure rises to 100/80.

Working Example V

A 55-year-old farmhand presents with a 3×8 centimeter irregular brown lesion on his forearm. The surrounding area shows changes typical of sun damage. A diagnosis of melanoma is made on biopsy. Immunochemistry shows high expression of nitric oxide synthase in the cells. Paraquat 10 mM is topically applied three times a day. Over the following week, the lesion decreases in size to 2×3 centimeters. The mass is then excised and the markings are shown to be clean.

Working Example VI

A mouth lesion is noted in a 60-year-old smoker during a routine dental visit. The lesion is found to be a squamous cell carcinoma. Histologic analysis shows high level expression of NOS and significant angiogenesis. The patient is given a 5 cc solution of paraquat swish and spit (at a dose of 100 $\mu$M). After seven days the tumor is found to have regressed. Because of some complicating oral ulcerations, the dose is decreased to 10 $\mu$M a day.

Working Example VII

A 40-year-old female is given the anti-tumor agent 5,6 dimethylxanthemone-4-acetic acid (5,6 MEXAA) to treat a solid tumor identified by biopsy on the left lower extremity, and lung. Treatment for seven days leads to an increase in nitric oxide synthase expression in the tumor on biopsy. At this time, the patient is treated with intravenous infusion of paraquat (4 milligram per kilogram) for seven cycles. After two weeks the tumor regresses and is not longer detectable.

Working Example VIII

A 55-year-old white male undergoes angioplasty of the left anterior descending coronary artery. Two weeks following procedure, he presents with chest pain and the radiographic evidence of restenosis. He undergoes repeat angioplasty with infusion of paraquat (dosage of 10 mg), locally instilled under pressure via the balloon. The patient does well without further episode of restenosis or angina.

Working Example IX

A 39-year-old white female with metastatic breast cancer receives adriamycin in the standard regimen. She develops light sensitivity and shortness of breath. An echocardiogram shows an ejection fraction at 35%. She is begun on the nitric oxide synthase inhibitor L-NAME 0.5 milligrams per kilogram per minute and her systolic blood pressure is then titrated to 100–120 mm Hg. Over the following two weeks, her ejection fraction improves to 50% and the drug is stopped.

Working Example X

A 70-year-old black male with middle cerebral arterial embolic stroke presents to the Emergency Room unconscious. He receives an infusion of L-monomethyl-L-arginine 10 mg IV bolus followed by 4.5 mg per kilogramper minute without improvement. After 30 minutes the therapy is stopped and he receives L-NAME at the same dose. Over the following day, the patient regains consciousness.

Working Example XI

A 62-year-old woman presents with breast cancer and is treated with standard regimen including adriamycin. The tumor fails to respond. She is given an infusion of a temperature-sensitive liposome encapsulated nitric oxide synthase, which is released in to the tumor by local heat (40–42° centigrate). The adriamycin infusion is then started and the tumor is shown to regress after six cycles of therapy.

Working Example XII

The adriamycin infusion in Example X after liposome encapsulated nitric oxide synthase treatment is replaced by 2 mg per day of diquat for six days. The tumor is shown to regress.

Working Example XIII

A 65-year-old accident victim presents with a blood pressure of 80/60 and a hematocrit of 20. He is bleeding profusely from an abdominal would and doctors are having difficulty maintaining his blood pressure with fluid resuscitation. He is begun on an intravenous drip of paraquat of 0.4 milligrams per kilogram over 2 hours. The blood pressure increases to 100/70 and the patient is stabilized.

Working Example XIV

A 60-year-old patient with congestive heart failure and COPD presents acutely short of breath. He is intubated for respiratory failure. A injection fraction shows an EF of 30% and a chest X-ray reveals pulmonary edema. His FEV1 is 0.8. The patient has a protracted hospital course and attempts to wean him from the ventilator are unsuccessful. He is then started on 10 milligram per kilogram IV bolus of L-NMMA and an intravenous drip at 0.5 milligrams per kilograms per minute. He is weaned from the ventilator over the following day.

Variations

Many variations of the above will be obvious to those skilled in the art. Thus, the invention is defined by the claims.

What is claimed is:

1. A method for treating paraquat-induced injury in a patient having such injury or for preventing paraquat-induced injury in a patient at risk for such comprising administering to said patient a therapeutically effective amount of a nitric oxide synthase inhibitor that blocks electron transfer reactions of nitric oxide synthase.

2. The method of claim 1 wherein the nitric oxide synthase inhibitor is L-nitroarginine methyl ester.

3. A method for treating paraquat-induced injury in a patient having such injury or for preventing paraquat-induced injury in a patient at risk for such comprising administering to said patient a therapeutically effective amount of NO providing compound.

4. The method of claim 3 wherein the compound is NO.

5. A method for treating a patient having a disease in which nitric oxide synthase contributes to reactive oxygen production which causes tissue injury, comprising administering to said patient a therapeutically effective amount of nitric oxide synthase inhibitor that blocks electron transfer reactions of nitric oxide synthase and of NO providing compound.

6. The method of claim 5 wherein the disease is a stroke.

7. The method of claim 5 wherein a single compound is administered as both the nitric oxide synthase inhibitor and the NO providing compound.

8. The method of claim 7 wherein the single compound is selected from the group consisting of NO-derivatized L-NAME.

9. A method for treating a patient having a disease where treatment with nitric oxide synthase inhibitor ameliorates symptoms of the disease but lowers the NO level to a cytotoxic level, or where it is beneficial to supplement treatment with nitric oxide synthase inhibitor with treatment with NO providing compound, comprising administering to said patient the nitric oxide synthase inhibitor in therapeutically effective amount and also a therapeutically effective amount of NO providing compound.

10. The method of claim 9 where the disease is selected from the group consisting of sepsis, stroke and adult respiratory distress syndrome.

11. The method of claim 9 wherein a single compound is administered as both the nitric oxide synthase inhibitor and the NO providing compound.

12. The method of claim 11 where the single compound is selected from the group consisting of NO-derivatized L-NAME.

13. A method for treating a patient with a disease characterized by pathologically proliferating cells containing nitric oxide synthase, comprising administering to said patient a therapeutically effective amount of a dipyridinium compound that is reduced by nitric oxide synthase.

14. The method of claim 13 wherein the pathologically proliferating cells constitute a tumor which is a high grade tumor.

15. The method of claim 14 wherein the dipyridinium compound is paraquat.

16. The method of claim 13 wherein agent that induces expression of nitric oxide synthase is also administered.

17. A method of treating a patient affected with a disorder in which reactive oxygen species contribute to pathology, comprising administering to said patient a therapeutically effective amount a nitric oxide synthase inhibitor which blocks generation of reactive oxygen species from NOS.

18. The method of claim 17 wherein the disorder is selected from the group consisting of paraquat-induced injury, stroke and adriamycin toxicity.

19. The method of claim 18 wherein the nitric oxide synthase inhibitor is L-nitroarginine methyl ester.

20. A method for inhibiting nitric oxide synthase in a patient in need thereof comprising administering to said patient a therapeutic amount of agent with a redox potential greater than nitric oxide synthase and an $LD_{50}$ greater than 1 $\mu$M to inhibit nitric oxide synthase, and optionally to provide therapeutic benefit except required in those cases necessary for novelty therapeutic amount of NO providing compound.

21. The method of claim 20 wherein the patient is affected with a disorder characterized by pathologically proliferating cells containing nitric oxide synthase and the agent in inhibiting nitric oxide synthase accepts electrons from it to generate reactive oxygen species to kill the pathologically proliferating cells.

22. The method of claim 21 wherein the pathologically proliferating cells constitute a tumor which is a high grade tumor.

23. The method of claim 20 wherein the patient is affected with a disorder characterized by pathologically proliferating cells containing nitric oxide synthase and the agent is selected from the group consisting of diquat, paraquat, lucigenin, Azure A, Azure B, Azure C, pyocyanin, acriflavine, lynasine, phenacridine, arninochromes, palmatine and homiclium.

24. The method of claim 20 wherein the agent is a dipyridinium compound which does not contain acylamino substituent.

25. The method of treating a patient affected with pathologically proliferating cells containing a diaphorase, comprising administering to said patient agent with a redox potential greater than the diaphorase and an $LD_{50}$ greater than 1 $\mu$M to generate reactive oxygen species and kill the pathologically proliferating cells, and optionally to provide therapeutic effect except required in those cases where necessary to provide novelty therapeutic amount of NO providing compound.

26. The method of claim 25 wherein the pathologically proliferating cells are causing restenosis.

27. The method of claim 26 wherein the agent is selected from the group consisting of methylene blue, ellipticinium, acridine, phenazine, adriamycin, quinones, dipyridinium compounds, Azure A, Azure B, Azure C, pyocyanin, acriflavine, lynasine, phenacridine, aminochromes, palmatine and homiclium.

28. A method of treating a patient affected with pathologically proliferating cells, comprising causing overexpression of nitric oxide synthase in said patient and administering to said patient a therapeutic amount of agent with redox potential greater than nitric oxide synthase and an $LD_{50}$ greater than 1 $\mu$M.

29. The method of claim 28 wherein the agent is paraquat.

30. A method of treating a patient in need of constricting of blood vessels, said method comprising administering to said patient a therapeutically effective amount of agent with redox potential greater than nitric oxide synthase and an $LD_{50}$ greater than 1 $\mu$M, and optionally to provide therapeutic effect except required in those cases necessary to provide novelty a therapeutic amount of NO providing compound.

31. The method of claim 30 wherein the patient is hypotensive.

32. The method of claim 31 wherein the agent is a dipyridinium compound which does not have an acylamino substituent.

33. The method of claim 32 wherein the agent is paraquat.

34. A method for treating a patient for a disorder where generation of $O_2^-$ provides benefit, comprising administering to said patient an amount of agent with redox potential greater than nitric oxide synthase and an $LD_{50}$ greater than 1 $\mu$M to generate $O_2^-$ from nitric oxide synthase or therapeutic amount of other agent which generates $O_2^-$ from nitric oxide synthase in the patient, and optionally to provide therapeutic effect except required in those cases necessary to provide novelty therapeutic amount of NO providing compound.

35. A method of determining nitric oxide synthase containing cells comprising the steps of adding a superoxide generating sufficient amount of paraquat to a suspension of cells and assaying for superoxide, with detecting of superoxide in the assay indicating the presence of nitric oxide synthase-containing cells.

36. A method for determining nitric oxide synthase deficient cells and thereby selecting for them, comprising adding paraquat to a suspension of cells in an amount to provide a concentration of paraquat ranging from 25 $\mu$M to 8 mM, thereby to kill nitric oxide synthase-containing cells and leave nitric oxide synthase deficient cells.

* * * * *

UNITED STATES PATENT AND TRADEMARK OFFICE
CERTIFICATE OF CORRECTION

PATENT NO. : 6,231,894 B1  
DATED : May 15, 2001  
INVENTOR(S) : Jonathan S. Stamler et al.

Page 1 of 1

It is certified that error appears in the above-identified patent and that said Letters Patent is hereby corrected as shown below:

<u>Claim 23, column 22,</u>
Line 25, change "arninochromes" to -- aminochromes --.

Signed and Sealed this

Eleventh Day of September, 2001

Attest:

*Nicholas P. Godici*

*Attesting Officer*

NICHOLAS P. GODICI  
*Acting Director of the United States Patent and Trademark Office*